United States Patent
Kapoor et al.

(10) Patent No.: US 9,289,392 B2
(45) Date of Patent: Mar. 22, 2016

(54) EXTENDED RELEASE PHARMACEUTICAL COMPOSITION OF ENTACAPONE OR SALTS THEREOF

(75) Inventors: Ritesh Kapoor, Mandi (IN); Munish Talwar, Panchkula (IN); Sanjay Mate, Pune (IN); Manoj Mashalkar, Latur (IN); Girish Kumar Jain, Delhi (IN); Mandar Kodgule, Mumbai (IN)

(73) Assignee: Wockhardt Ltd., Bandra East, Mumbai (IN)

( * ) Notice: Subject to any disclaimer, the term of this patent is extended or adjusted under 35 U.S.C. 154(b) by 763 days.

(21) Appl. No.: 13/060,109

(22) PCT Filed: Aug. 22, 2009

(86) PCT No.: PCT/IB2009/053698
§ 371 (c)(1),
(2), (4) Date: May 18, 2011

(87) PCT Pub. No.: WO2010/020969
PCT Pub. Date: Feb. 25, 2010

(65) Prior Publication Data
US 2011/0229561 A1    Sep. 22, 2011

(30) Foreign Application Priority Data

Aug. 22, 2008 (IN) .......................... 1777/MUM/2008
Aug. 22, 2008 (IN) .......................... 1778/MUM/2008

(51) Int. Cl.
| | | |
|---|---|---|
| *A61K 9/48* | (2006.01) | |
| *A61K 9/20* | (2006.01) | |
| *A61K 9/24* | (2006.01) | |
| *A61K 31/198* | (2006.01) | |
| *A61K 31/277* | (2006.01) | |

(52) U.S. Cl.
CPC ............... *A61K 9/2054* (2013.01); *A61K 9/209* (2013.01); *A61K 9/2027* (2013.01); *A61K 31/198* (2013.01); *A61K 31/277* (2013.01)

(58) Field of Classification Search
CPC ... A61K 9/2027; A61K 9/2054; A61K 9/209; A61K 31/198; A61K 31/277; A61K 2300/00
See application file for complete search history.

(56) References Cited

U.S. PATENT DOCUMENTS

| | | | | |
|---|---|---|---|---|
| 6,500,867 | B1 * | 12/2002 | Virkki et al. ............ | 514/646 |
| 6,599,530 | B2 | 7/2003 | Vahervuo | |
| 2007/0275060 | A1 | 11/2007 | Befumo | |
| 2008/0118556 | A1 * | 5/2008 | Devane et al. ............ | 424/456 |

FOREIGN PATENT DOCUMENTS

| | | |
|---|---|---|
| WO | WO2006/131591 A2 | 12/2006 |
| WO | WO2007/073702 A2 | 7/2007 |
| WO | WO2008053297 A2 | 5/2008 |
| WO | WO2009/098661 A1 | 8/2009 |

OTHER PUBLICATIONS

Bet et al ("Bimodal administration of entacapone in Parkinson's disease patients improves motor control," European Journal of Neurology 2008, 15:268-273 (available online Feb. 14, 2008)).*
Chhipa et al "Formulation Optimization of Sustained Release Pellets of Itopride Hydrochloride using Different Polymers," Journal of Pharmacy Research 2009 2(8) 1404-1408).*

* cited by examiner

*Primary Examiner* — Suzanne Ziska
(74) *Attorney, Agent, or Firm* — Bio Intellectual Property Services (Bio IPS) LLC; O. Sam Zaghmout

(57) ABSTRACT

There is provided an extended release pharmaceutical composition comprising from about 200 mg to about 1000 mg of entacapone or salts thereof, optionally with other pharmaceutically acceptable excipients. The invention also provides an extended release pharmaceutical composition comprising triple combination of from about 30 mg to about 300 mg of levodopa, 10 mg to about 100 mg of carbidopa and 200 mg to about 1000 mg of entacapone or salts thereof, optionally with other pharmaceutically acceptable excipients. The invention also relates to process of preparation of such compositions.

15 Claims, No Drawings

EXTENDED RELEASE PHARMACEUTICAL COMPOSITION OF ENTACAPONE OR SALTS THEREOF

FIELD OF THE INVENTION

There is provided an extended release pharmaceutical composition comprising from about 200 mg to about 1000 mg of entacapone or salts thereof, optionally with other pharmaceutically acceptable excipients. The invention also provides an extended release pharmaceutical composition comprising triple combination of from about 30 mg to about 300 mg of levodopa, 10 mg to about 100 mg of carbidopa and 200 mg to about 1000 mg of entacapone or salts thereof, optionally with other pharmaceutically acceptable excipients. The invention also relates to process of preparation of such compositions.

BACKGROUND OF THE INVENTION

Entacapone, an inhibitor of catechol-O-methyltransferase (COMT), used in the treatment of Parkinson's disease as an adjunct to levodopa/carbidopa therapy. The chemical name of entacapone is (E)-2-cyano-3-(3,4-dihydroxy-5-nitrophenyl)-N,N-diethyl-2-propenamide. Its empirical formula is $C_{14}H_{15}N_3O_5$, and its structural formula is:

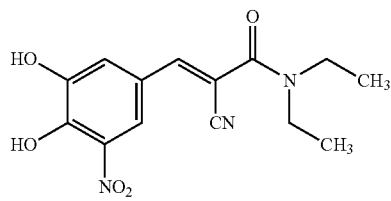 [SMILES: CCN(CC)C(=O)/C(C#N)=C/c1cc(O)c(O)c([N+](=O)[O-])c1]

Carbidopa, an inhibitor of aromatic amino acid decarboxylation, is a white, crystalline compound, slightly soluble in water. It is designated chemically as (−)-L-(α-hydrazino-(α-methyl-β-(3,4-dihydroxybenzene) propanoic acid. Its empirical formula is $C_{10}H_{14}N_2O_4$ and its structural formula is:

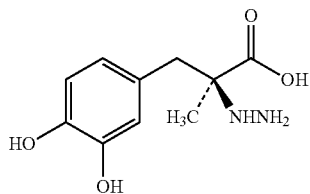 [SMILES: C[C@@](Cc1ccc(O)c(O)c1)(NN)C(=O)O]

Levodopa, an aromatic amino acid, is a white, crystalline compound, slightly soluble in water. It is designated chemically as (−)-L-α-amino-β-(3,4-dihydroxybenzene) propanoic acid. Its empirical formula is $C_9H_{11}NO_4$, and its structural formula is:

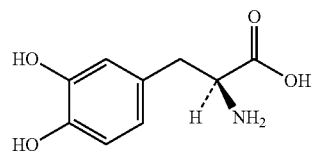 [SMILES: N[C@@H](Cc1ccc(O)c(O)c1)C(=O)O]

U.S. Pat. No. 6,599,530 provides oral compacted compositions of entacapone or salt thereof with pharmaceutically acceptable excipients.

U.S. Pat. No. 5,446,194 provides entacapone or pharmaceutically acceptable salts or esters thereof.

U.S. Pat. Nos. 6,500,867 and 6,797,732 provide oral solid tablet compositions comprising entacapone, levodopa and carbidopa, or pharmaceutically acceptable salts or hydrates thereof, and a pharmaceutically acceptable excipient.

U.S. Pat. No. 7,094,427 and US Publication No 20040166159 provide a composition comprising immediate release and controlled release component.

US Publication No 20080051459 provide a method of treating Parkinson's disease comprising administering pharmaceutically effective amount of a composition comprising levodopa.

US Publication No 20070275060 provide an extended release tablet comprising an extended release composition comprising levodopa; and an immediate or rapid release composition comprising carbidopa.

US Publication No 20060173074 provides a method for treatment of restless legs syndrome in a mammal.

PCT Publication No. 07/073,702 provides a multi-layered tablet providing three different release profiles.

Entacapone is available as immediate release composition under the trade name Comtan®. The marketed strength is 200 mg.

The triple combination of levodopa, carbidopa and entacapone is available as immediate release composition in different strengths. For example Stalevo® 50 (containing 12.5 mg of carbidopa, 50 mg of levodopa and 200 mg of entacapone), Stalevo® 75 (containing 18.75 mg of carbidopa, 75 mg of levodopa and 200 mg of entacapone), Stalevo® 100 (containing 25 mg of carbidopa, 100 mg of levodopa and 200 mg of entacapone), Stalevo® 125 (31.2575 mg of carbidopa, 125 mg of levodopa and 200 mg of entacapone), Stalevo® 150 (containing 37.5 mg of carbidopa, 150 mg of levodopa and 200 mg of entacapone) and Stalevo® 200 (containing 50 mg of carbidopa, 200 mg of levodopa and 200 mg of entacapone).

Parkinson's disease is a slowly progressive disease, in which the symptoms get worse over time. Therefore, the symptoms will change and evolve. The pattern of symptoms can vary for each person. Over a number of years, however, some people may see changes in the way their medication controls their symptoms. These changes are commonly known as motor fluctuations. Over time, symptoms begin to come back before it is time to take next dose of levodopa medication. This change in symptoms is called "wearing-off." As "wearing-off" becomes more noticeable, the amount of time for a good response to levodopa (known as "on" time) shortens and the time for poor response to levodopa (known as "off" time) may lengthen.

In the early stages of the disease, the brain is able to store enough dopamine. This permits smoother release of dopamine in the brain. It also provides a more constant control of symptoms. However, as Parkinson's disease gets worse, the brain has fewer cells that can take up levodopa and store it as dopamine for release when levels are low. Because of this reduced ability to store dopamine in the brain, symptoms may return after shorter periods of time (e.g. "wearing-off"). If someone with a reduced ability to store dopamine is given too much levodopa, it may lead to side effects (e.g. dyskinesia).

It may be possible to better control these symptoms by changing or adjusting the treatment. As these motor fluctuations emerge, other unwanted side effects may occur. These include involuntary movements, known as dyskinesia (e.g. twisting/turning movements) or dystonia (e.g. prolonged muscle cramping). The patients treated for Parkinson's disease may frequently develop motor fluctuations characterized by end-of-dose failure, peak dose dyskinesia and akinesia, with levodopa therapy ("wearing off") in which the patient suffers from unpredictable swings from mobility to immobility. More than 50% of patients with Parkinson's disease develop motor response fluctuations (the 'wearing off' phenomenon) after treatment with levodopa therapy. Symptoms of wearing off include bradykinesia, dystonia, tremors, decreased manual dexterity, paresthesia, muscle pain, voice softness.

It is believed that the 'wearing off' effect can be minimized in patients with a treatment regimen, which provides less rapid dissolution properties and providing a more even plasma level profile of levodopa. When administered in conjunction with levodopa, entacapone increases the bioavailability of levodopa by facilitating its passage across the blood-brain barrier. Hence, entacapone is approved as an adjunct to levodopa therapy in Parkinson's disease. However, the dosage of currently available formulation of Entacapone is eight times a day for 200 mg tablets. The frequent dosing of these formulations is associated with more fluctuating plasma entacapone concentrations. Further, this regimen is not patient compliant. Another problem with entacapone formulations is for the patients having swallowing problems. These patients cannot easily swallow the tablet.

Further, it has been observed that it is very inconvenient for the patient to take a tablet of Sinemet CR and Comtan simultaneously number of times a day, which leads to patient non-compliance especially in Parkinson's patient. Further, literature also suggests when the three ingredients are present together vis a vis entacapone, carbidopa and levodopa, it leads to decrease in bioavailability of entacapone and levodopa. Therefore, the marketed formulation Stalevo contains substantial portion of carbidopa separate from levodopa and carbidopa. Additionally, literature also reports destabilization of triple combination formulation in presence of microcrystalline cellulose.

Hence, there is a need for patient compliant entacapone composition and/or triple combination comprising levodopa, carbidopa and entacapone that will dissolve slowly and provide a more even plasma level profile in patients with entacapone or levodopa/entacapone/carbidopa treatment regimen.

SUMMARY OF THE INVENTION

In one of the aspects of the invention there is provided a pharmaceutical composition comprising from about 200 to about 1000 mg of entacapone or salts thereof, optionally with other pharmaceutically acceptable excipients.

In another general aspect of the invention there is provided a pharmaceutical composition comprising from about 200 to about 1000 mg of entacapone or salts thereof, optionally with other pharmaceutically acceptable excipients, wherein one tablet of said composition exhibits no significant difference in rate and/or extent of absorption of entacapone as compared to 2-4 tablets of 200 mg of immediate release entacapone commercially marketed as Comtan® administered at the interval of 3-4 hours.

In another general aspect of the invention there is provided a method of treating Parkinson's disease in a mammal, comprising administering to a mammal in need thereof, an extended release pharmaceutical composition comprising from about 200 to about 1000 mg of entacapone or salts thereof in a mammal in need thereof, optionally with other pharmaceutically acceptable excipients.

In another general aspect of the invention there is provided a method of treating Parkinson's disease in a mammal, comprising administering to a mammal in need thereof, an extended release pharmaceutical composition comprising from about 200 to about 1000 mg of entacapone or salts there of in a mammal in need thereof, optionally with other pharmaceutically acceptable excipients, wherein one tablet of the said composition exhibits no significant-difference in rate and/or extent of absorption of entacapone as compared to 2-4 tablets of 200 mg of immediate release entacapone commercially marketed as Comtan® administered at the interval of 3-4 hours.

In another general aspect of the invention there is provided a method of reducing the "wearing off" phenomena in Parkinson's patients, comprising administering to patient in need thereof, an extended release pharmaceutical composition comprising from about 200 to about 1000 mg of entacapone or salts there of in a mammal in need thereof, optionally with other pharmaceutically acceptable excipients.

In another general aspect of the invention there is provided a method of reducing the "wearing off" phenomena in Parkinson's patients, comprising administering to patient in need thereof, an extended release pharmaceutical composition comprising from about 200 to about 1000 mg of entacapone or salts there of in a mammal in need thereof, optionally with other pharmaceutically acceptable excipients, wherein one tablet of the said composition exhibits no significant difference in rate and/or extent of absorption of entacapone as compared to 2-4 tablets of 200 mg of immediate release entacapone commercially marketed as Comtan® administered at the interval of 3-4 hours.

In another general aspect of the invention there is provided a process for preparing a pharmaceutical composition comprising from about 200 to about 1000 mg of entacapone or salts thereof, wherein the said process comprises of coating or mixing entacapone with one or more pharmaceutically acceptable polymers, optionally with other pharmaceutical excipients and converting the mixture into suitable dosage form.

In another general aspect of the invention there is provided an extended release pharmaceutical composition comprising from about 200 to about 1000 mg of entacapone or salts thereof, wherein the said composition exhibits a dissolution profile such that within 60 minutes at least 15% of entacapone is released, wherein the release rate is measured in Apparatus 2 (USP, Dissolution, paddle, 75 rpm) using 1000 ml of pH 5.5 phosphate buffer at 37° C.±0.5° C.

In another general aspect of the invention there is provided an extended release pharmaceutical composition comprising from about 200 to about 1000 mg of entacapone or salts thereof, wherein the said composition exhibits a dissolution profile such that within 4 hrs at least 60% of entacapone is released, wherein the release rate is measured in Apparatus 2 (USP, Dissolution, paddle, 75 rpm) using 1000 ml of pH 5.5 phosphate buffer at 37° C.±0.5° C.

In another general aspect of the invention there is provided a pharmaceutical composition comprising from about 30 mg to about 300 mg of levodopa, 10 mg to about 100 mg of carbidopa and 200 mg to about 1000 mg of entacapone or salts thereof, optionally with other pharmaceutically acceptable excipients.

In another general aspect of the invention there is provided a method of treating Parkinson's disease in a mammal, comprising administering to a mammal in need thereof, an extended release pharmaceutical composition comprising from about 30 mg to about 300 mg of levodopa, 10 mg to about 100 mg of carbidopa and 200 mg to about 1000 mg of entacapone or salts thereof, optionally with other pharmaceutically acceptable excipients.

In another general aspect of the invention there is provided a method of treating Parkinson's disease in a mammal, comprising administering to a mammal in need thereof, an extended release pharmaceutical composition comprising from about 30 mg to about 300 mg of levodopa, 10 mg to about 100 mg of carbidopa and 200 mg to about 1000 mg of entacapone or salts thereof, optionally with other pharmaceutically acceptable excipients, wherein one tablet of the said composition exhibits no significant difference in rate and/or extent of absorption of entacapone, levodopa and carbidopa as compared to 2-4 tablets of immediate release entacapone, levodopa and carbidopa formulation commercially marketed as Stalevo® administered at the interval of 3-4 hours.

In another general aspect of the invention there is provided a method of reducing the "wearing off" phenomena in Parkinson's patients, comprising administering to patient in need thereof, an extended release pharmaceutical composition comprising from about 30 mg to about 300 mg of levodopa, 10 mg to about 100 mg of carbidopa and 200 mg to about 1000 mg of entacapone or salts thereof, optionally with other pharmaceutically acceptable excipients.

In another general aspect of the invention there is provided an extended release pharmaceutical composition comprising from about 30 mg to about 300 mg of levodopa, 10 mg to about 100 mg of carbidopa and 200 mg to about 1000 mg of entacapone or salts thereof, wherein said composition exhibits a dissolution profile such that within 60 minutes at least 15% of entacapone or at least 15% of levodopa or at least 15% of carbidopa is released, wherein the release rate is measured in Apparatus 2 (USP, Dissolution, paddle, 75 rpm) using 1000 ml of pH 5.5 phosphate buffer at 37° C.±0.5° C.

In another general aspect of the invention there is provided an extended release pharmaceutical composition from about 30 mg to about 300 mg of levodopa, 10 mg to about 100 mg of carbidopa and 200 mg to about 1000 mg of entacapone or salts thereof, wherein said composition exhibits a dissolution profile such that within 4 hrs at least 60% of entacapone or at least 60% of levodopa or at least 60% of carbidopa is released, wherein the release rate is measured in Apparatus 2 (USP, Dissolution, paddle, 75 rpm) using 1000 ml of pH 5.5 phosphate buffer at 37° C.±0.5° C.

In another general aspect of the invention there is provided a process for preparing an extended release pharmaceutical composition from about 30 mg to about 300 mg of levodopa, 10 mg to about 100 mg of carbidopa and 200 mg to about 1000 mg of entacapone or salts thereof, wherein the said process comprises of coating or mixing one or more of levodopa, carbidopa and entacapone with one or more pharmaceutically acceptable polymers, optionally mixing with other pharmaceutically acceptable excipients and converting into suitable dosage form.

Embodiments of the pharmaceutical composition may include one or more of the following features. For example, the pharmaceutically acceptable excipients may include one or more of fillers, binders, lubricants, sweeteners, coloring and flavoring agents, glidants, disintegrants, and the like.

The details of one or more embodiments of the inventions are set forth in the description below. Other features, objects and advantages of the inventions will be apparent from the description and claims.

DETAILED DESCRIPTION OF THE INVENTION

The inventors while working on the entacapone formulation have noticed that when entacapone is formulated in an extended release form, it allows for the continuous release of entacapone over a prolonged period. Extended release entacapone composition maintains controlled release of entacapone thereby leading to non-fluctuating constant plasma levels of entacapone. This further leads to reduction in the "wearing-off" phenomena, which is observed in Parkinson's patients due to fluctuating plasma levels.

The inventors have also noticed that when entacapone or levodopa or carbidopa is formulated in triple combination extended release form, it allows for the continuous release of entacapone or levodopa or carbidopa over a prolonged period. Extended release composition maintains controlled release of entacapone, levodopa and carbidopa thereby leading to non-fluctuating constant plasma levels of entacapone, levodopa and carbidopa. This further leads to reduction in the "wearing-off" phenomena, which is observed in Parkinson's patients due to fluctuating plasma levels.

The term 'extended release' as used herein refers to specific release of drug over a specified time period, which may extend from about 4 hrs to about 24 hrs or more.

The extended release in the pharmaceutical composition may be achieved by one or more of coating or embedding in matrix using with hydrophilic or hydrophobic polymers or by attachment to ion-exchange resins. Further, extended release may be achieved by osmotic oral release technology also.

One tablet of the composition of the invention is bioequivalent to 2-4 tablets of 200 mg of immediate release entacapone commercially marketed as Comtan®, when commercially available tablets are administered within at the interval of 3-4 hours.

One tablet of the composition of the invention exhibits no significant difference in rate and/or extent of absorption of entacapone, levodopa and carbidopa as compared to 2-4 tablets of immediate release entacapone, levodopa and carbidopa formulation commercially marketed as Stalevo® administered at the interval of 3-4 hours.

"Bioequivalency" is established by a 90% Confidence Interval (CI) of between 0.80 and 1.25 for both $C_{max}$ and AUC under USFDA regulatory guidelines, or a 90% CI for AUC of between 0.80 to 1.25 and a 90% CI for $C_{max}$ of between 0.70 to 1.43 under the European EMEA regulatory guidelines.

The term "confidence interval" as used herein refers to plain meaning known to ordinary skill in the art. Confidence interval refers to a statistical range with a specified probability that a given parameter lies within the range.

The term "covariance" as used herein refers to plain meaning known to ordinary skill in the art. It is a statistical measure of the variance of two random variables that are observed or measured in the same mean time period. This measure is equal to the product of the deviations of corresponding values of the two variables from their respective means.

The extended release pharmaceutical composition may include one or more of tablet, bilayered tablet, trilayered tablet, capsule, powder, disc, caplet, granules, pellets, granules in capsule, minitablets, minitablets in capsule, pellets in capsule, sachet and the like.

The amount of entacapone in these pharmaceutical compositions varies from about 200 to about 1000 mg. The amount of levodopa in these pharmaceutical compositions varies from about 30 to about 300 mg. The amount of carbidopa in these pharmaceutical compositions varies from about 10 to about 100 mg.

The extended release composition comprising triple combination of levodopa, carbidopa, entacapone, wherein at least one of levodopa, entacapone or carbidopa is in extended release form.

Suitable hydrophilic or hydrophobic polymers comprise one or more of polyvinyl acetate, cellulose acetate, cellulose acetate butyrate, cellulose acetate propionate, ethyl cellulose, a fatty acid, a fatty acid ester, an alkyl alcohol, a wax, shellac, rosin, zein (prolamine from corn), povidone, kollidon SR, a poly(meth)acrylate, microcrystalline cellulose or poly(ethylene oxide), polyuronic acid salts, cellulose ethers, xanthan gum, tragacanth gum, gum karaya, guar gum, acacia, gellan gum locust bean gum, alkali metal salts of alginic acid or pectic acid, sodium alginate, potassium alginate, ammonium alginate, hydroxypropyl cellulose, hydroxy ethyl cellulose, hydroxypropyl methyl cellulose, carboxyvinyl polymers, polymerized gelatin, shellac, methacrylic acid copolymer type C NF, cellulose butyrate phthalate, cellulose hydrogen phthalate, cellulose propionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethyl cellulose (CMEC), hydroxypropyl methylcellulose acetate succinate (HPMCAS), and acrylic acid polymers and copolymers like methyl acrylate, ethyl acrylate, methyl methacrylate and/or ethyl methacrylate with copolymers of acrylic and methacrylic acid esters (Eudragit NE, Eudragit RL, Eudragit RS) and the like. Polymer may be used from 0.1-50% by weight of the composition.

The extended release pharmaceutical composition may comprise one or more pharmaceutically acceptable excipients. The pharmaceutically acceptable excipients may include diluents, binders, disintegrants, lubricants, glidants and the like.

Suitable binder may be one or more of, povidone, starch, stearic acid, gums, hydroxypropylmethyl cellulose and the like. Binder may be used from 0.1% to 40% by weight of the composition Suitable diluent may be one or more of, microcrystalline cellulose, mannitol, calcium phosphate, calcium sulfate, kaolin, dry starch, powdered sugar and the like. Diluent may be used from 1 to 50% by weight of the composition.

Suitable disintegrant may be one or more of starch, croscarmellose sodium, crospovidone, sodium starch glycolate and the like. Disintegrant may be used from 2-20% by weight of the composition.

Suitable lubricant may be one or more of magnesium stearate, zinc stearate, calcium stearate, stearic acid, sodium-stearyl fumarate, hydrogenated vegetable oil, glyceryl behenate and the like. Lubricant may be used from 0.1-5% by weight of the composition.

Suitable glidant may be one or more of colloidal silicon dioxide, talc or cornstarch and the like. Glidant may be used from 0.1-5% by weight of the composition.

The pharmaceutical composition may be prepared by mixing entacapone with one or more pharmaceutically acceptable polymers, mixing with other pharmaceutically acceptable excipients and converting into suitable dosage form The pharmaceutical composition may also be prepared by mixing entacapone, levodopa and carbidopa with one or more pharmaceutically acceptable polymers, mixing with other pharmaceutically acceptable excipients and converting into suitable dosage form.

The invention is further illustrated by the following examples which are provided merely to be exemplary of the invention and do not limit the scope of the invention. Certain modifications and equivalents will be apparent to those skilled in the art and are intended to be included within the scope of the invention.

EXAMPLES

The composition of batches is provided in Table 1 to 23. Following formulations are representatives of the preferred compositions of the invention. The preparation of example is detailed below.

Example-I

TABLE 1

Pharmaceutical composition of the invention

| Ingredients | % w/w |
| --- | --- |
| Entacapone | 60.1 |
| Mannitol | 18.0 |
| Hydroxypropyl methyl cellulose | 16.2 |
| Povidone | 0.9 |
| Magnesium Stearate | 0.9 |
| Talc | 0.2-3 |
| Coating | |
| Opadry | 3.8 |

Procedure:

Entacapone and mannitol were sifted and co-sifted through mesh to form a bulk. Hydroxypropyl methyl cellulose was sifted and added to the above bulk to form a mixture. A part of magnesium stearate was sifted and mixed with the above mixture to form a bulk. The bulk was dry granulated using roller compactor to form the slugs. The slugs were size reduced to form granules. The granules were lubricated with remaining portion of magnesium stearate and talc to form a blend. The blend was compressed using suitable tooling to form tablets. The tablets were coated using Opadry.

TABLE 2

Dissolution data of composition prepared as per example I.

| Time (hrs) | % drug released |
| --- | --- |
| 0.5 | 28 |
| 1 | 52 |
| 2 | 74 |
| 3 | 88 |
| 4 | 96 |

Table 2 provides the dissolution data of composition prepared as per formula given in table 1. For determination of drug release rate, USP Type 2 Apparatus (rpm 75) was used wherein 1000 ml of pH 5.5 phosphate buffer at 37° C.±0.5° C. was used as medium.

Example-II

TABLE 3

Pharmaceutical composition of the invention

| Ingredients | % w/w |
|---|---|
| Entacapone | 57.1 |
| Lactose | 19.3 |
| Hydroxy ethyl cellulose | 12.4 |
| Hydroxypropyl methyl cellulose | 8.6 |
| Water | q.s. |
| Magnesium Stearate | 1.4 |
| Talc | 1.1 |

Procedure: Entacapone, lactose, hydroxy ethyl cellulose and hydroxypropyl methylcellulose were co-sifted and mixed to form a bulk. The bulk was wet granulated using water to form the granules and the granules were dried. The dried granules were size reduced. Magnesium stearate and talc were sifted and added to the size reduced granules and were compressed using suitable tooling to form tablets.

TABLE 4

Dissolution data of composition prepared as per example II.

| Time (hrs) | % drug released |
|---|---|
| 0.5 | 33 |
| 1 | 58 |
| 2 | 78 |
| 3 | 88 |
| 4 | 97 |

Table 4 provides the dissolution data of composition prepared as per formula given in table 3. For determination of drug release rate, USP Type 2 Apparatus (rpm 75) was used wherein 1000 ml of pH 5.5 phosphate buffer at 37° C.±0.5° C. was used as medium.

Example-III

TABLE 5

Pharmaceutical composition of the invention

| Ingredients | % w/w |
|---|---|
| Entacapone | 74.1 |
| Microcrystalline cellulose | 10.7 |
| Kollidon SR | 13.3 |
| Magnesium Stearate | 1.1 |
| Talc | 0.7 |

Procedure: Entacapone, microcrystalline cellulose and kollidon SR were co-sifted and mixed to form a bulk. Magnesium stearate and talc were sifted to form a bulk separately. The two different bulks were mixed and compressed using suitable tooling to form tablets.

TABLE 6

Dissolution data of composition prepared as per example III.

| Time (hrs) | % drug released |
|---|---|
| 0.5 | 22 |
| 1 | 43 |
| 2 | 68 |
| 3 | 82 |
| 4 | 90 |

Table 6 provides the dissolution data of composition prepared as per formula given in table 5. For determination of drug release rate, USP Type 2 Apparatus (rpm 75) was used wherein 1000 ml of pH 5.5 phosphate buffer at 37° C.±0.5° C. was used as medium.

Example-IV

TABLE 7

Pharmaceutical composition of the invention

| Ingredients | % w/w |
|---|---|
| IR Layer | |
| Entacapone | 15.6 |
| Mannitol | 12.2 |
| Crospovidone | 3.8 |
| Povidone | 2.2 |
| Magnesium stearate | 0.6 |
| ER Layer | |
| Entacapone | 46.9 |
| Mannitol | 7.0 |
| Hydroxypropyl methyl cellulose | 10.2 |
| Magnesium Stearate | 0.8 |
| Talc | 0.8 |

Procedure: IR Layer Granules

Entacapone and mannitol were co-sifted to form a bulk. Crospovidone, povidone and a part of magnesium stearate were sifted and added to bulk and mixed to form a bulk. The bulk was dry granulated using roller compactor to form the slugs and the slugs were size reduced. The remaining portion of magnesium stearate to be added to size reduced granules and mixed.

ER Layer Granules

Entacapone and mannitol were co-sifted to form a bulk. Hydroxypropyl methylcellulose and a part of magnesium stearate were sifted and added to bulk and mixed to form a bulk. The above bulk was dry granulated using roller compactor to form the slugs and the slugs were size reduced. The remaining portion of magnesium stearate and talc were added to size reduced granules and mixed.

Compression

The IR layer and ER layer granules were compressed to form a bilayer tablet.

TABLE 8

Dissolution data of composition prepared as per example IV.

| Time (hrs) | % drug released |
|---|---|
| 0.5 | 23 |
| 1 | 44 |
| 2 | 71 |

TABLE 8-continued

Dissolution data of composition prepared as per example IV.

| Time (hrs) | % drug released |
|---|---|
| 3 | 84 |
| 4 | 92 |

Table 8 provides the dissolution data of composition prepared as per formula given in table 7. For determination of drug release rate, USP Type 2 Apparatus (rpm 75) was used wherein 1000 ml of pH 5.5 phosphate buffer at 37° C.±0.5° C. was used as medium.

Example-V

TABLE 9

Pharmaceutical composition of the invention

| Ingredients | % w/w |
|---|---|
| IR Layer | |
| Entacapone | 17.1 |
| Mannitol | 9.1 |
| Sodium starch Glycolate | 4.3 |
| Povidone | 2.1 |
| Water | q.s. |
| Magnesium stearate | 0.5 |
| ER Layer | |
| Entacapone | 51.3 |
| Mannitol | 8.0 |
| Povidone | 6.0 |
| Water | q.s. |
| Magnesium Stearate | 0.9 |
| Talc | 0.9 |

Procedure: IR Layer Granules

Entacapone, sodium starch glycolate and mannitol were co-sifted to form a bulk. Povidone was dissolved in water and the bulk was wet granulated with povidone solution to form granules and the granules were dried. The granules were size reduced. The size reduced granules were lubricated with magnesium stearate.

ER Layer Granules

Entacapone and mannitol were co-sifted to form a bulk. Povidone was dissolved in water and the bulk was wet granulated with povidone solution to form granules and the granules were dried. The granules were size reduced. The size reduced granules were lubricated with magnesium stearate and talc.

Compression

The IR layer and ER layer granules were compressed to form a bilayer tablet.

TABLE 10

Dissolution data of composition prepared as per example V.

| Time (hrs) | % drug released |
|---|---|
| 0.5 | 36 |
| 1 | 59 |
| 2 | 78 |
| 3 | 89 |
| 4 | 96 |

Table 10 provides the dissolution data of composition prepared as per formula given in table 9. For determination of drug release rate, USP Type 2 Apparatus (rpm 75) was used wherein 1000 ml of pH 5.5 phosphate buffer at 37° C.±0.5° C. was used as medium.

Example VI

TABLE 11

Pharmaceutical composition of the invention

| Ingredient | % w/w |
|---|---|
| IR Layer | |
| Entacapone | 4.98 |
| Mannitol 25 | 1.25 |
| Crospovidone | 0.60 |
| Povidone K30 | 0.45 |
| Mannitol SD 200 | 1.67 |
| Magnesium stearate | 0.07 |
| Talc | 0.12 |
| Magnesium stearate | 0.07 |
| ER Layer | |
| Entacapone | 44.83 |
| Mannitol 25 | 11.21 |
| Plasdone S630 | 4.48 |
| HPMC K 100LVP | 13.23 |
| Mannitol 25 | 3.81 |
| Magnesium stearate | 0.45 |
| Mannitol SD 200 | 10.09 |
| Magnesium stearate | 1.57 |
| Talc | 0.34 |
| Magnesium stearate | 0.78 |

Procedure: IR Layer Granules:

Entacapone and Mannitol were co-sifted to form a bulk. Crospovidone, Povidone K30, & Mannitol SD 200 were also co-sifted and mixed with above bulk. This bulk was lubricated by using magnesium stearate. Dry granulated this bulk and granules were prepared. Magnesium stearate & Talc were added to these prepared granules.

ER Layer Granules:

Entacapone and Mannitol were co-sifted to form a bulk. Plasdone S630, HPMC K100LVP and Mannitol were co-sifted and mixed with above bulk. This bulk was lubricated by using magnesium stearate. Dry granulated this bulk and granules were prepared. Magnesium stearate & Talc were added to these prepared granules.

Compression

The IR layer and ER layer granules were compressed to form a bilayer tablet.

TABLE 12

Dissolution data of composition prepared as per Example VI.

| Time (hrs) | % drug released |
|---|---|
| 0 | 0 |
| 0.5 | 27 |
| 1 | 34 |
| 2 | 45 |
| 3 | 57 |
| 4 | 72 |
| 5 | 91 |
| 6 | 93 |

Table 12 provides the dissolution data of composition prepared as per formula given in table 11. For determination of drug release rate, USP Type 2 Apparatus (rpm 75) was used wherein 1000 ml of pH 5.5 phosphate buffer at 37° C.±0.5° C. was used as medium.

TABLE 13

Bio Data (fed study)

| PK Parameters | Ratio % (T/R) | 90% C.I. Lower Limit | 90% C.I. Upper Limit | P-Value | Power (%) | MSE | Intra-CV (%) |
|---|---|---|---|---|---|---|---|
| Cmax | 91.35 | 87.83 | 95.08 | 0.0010 | 97.99% | 0.01851 | 13.58 |
| AUCt | 97.15 | 88.63 | 106.48 | 0.0011 | 98.74% | 0.01852305 | 13.67 |
| AUCinf | 97.21 | 88.69 | 106.55 | 0.0011 | 98.74% | 0.01852 | 13.67 |

Table 13 provides bio profile of entacapone ER tablets prepared as per example VI under fed condition versus Reference product Comtan® 200 mg. Study design include randomized, single dose, open-label, three-treatment, three-period, three-sequence, crossover comparative bioavailability study in 15 normal, adult, human subjects under fed condition.

Example VII

TABLE 14

Pharmaceutical composition of the invention

| Ingredient | % w/w |
|---|---|
| IR Layer | |
| Entacapone | 10.05 |
| Mannitol 25 | 2.51 |
| Crospovidone | 1.21 |
| Povidone K30 | 0.90 |
| Mannitol SD 200 | 3.37 |
| Magnesium stearate | 0.15 |
| Talc | 0.25 |
| Magnesium stearate | 0.15 |
| ER Layer | |
| Entacapone | 40.20 |
| Mannitol 25 | 10.05 |
| Plasdone S630 | 4.02 |
| HPMC K 100LVP | 11.86 |
| Mannitol 25 | 3.42 |
| Magnesium stearate | 0.40 |
| Mannitol SD 200 | 9.05 |
| Magnesium stearate | 0.30 |
| Talc | 0.70 |
| Magnesium stearate | 1.41 |

Procedure: IR Layer Granules:

Entacapone and Mannitol were co-sifted to form a bulk. Crospovidone, Povidone K30, & Mannitol SD 200 were also co-sifted and mixed with above bulk. This bulk was lubricated by using magnesium stearate. Dry granulated this bulk and granules were prepared. Magnesium stearate & Talc were added to these prepared granules.

ER layer Granules:

Entacapone and Mannitol were co-sifted to form a bulk. Plasdone S630, HPMC K100LVP and Mannitol were co-sifted and mixed with above bulk. This bulk was lubricated by using magnesium stearate. Dry granulated this bulk and granules were prepared. Magnesium stearate & Talc were added to these prepared granules.

Compression

The IR layer and ER layer granules were compressed to form a bilayer tablet.

TABLE 15

Dissolution data of composition prepared as per Example VII.

| Time (hrs) | % drug released |
|---|---|
| 0 | 0 |
| 0.5 | 31 |
| 1 | 42 |
| 2 | 55 |
| 3 | 63 |
| 4 | 74 |
| 5 | 86 |
| 6 | 95 |

Table 15 provides the dissolution data of composition prepared as per formula given in table 14. For determination of drug release rate, USP Type 2 Apparatus (rpm 75) was used wherein 1000 ml of pH 5.5 phosphate buffer at 37° C.±0.5° C. was used as medium.

Example-VIII

TABLE 16

Pharmaceutical composition of the invention

| Ingredients | % w/w |
|---|---|
| Entacapone | 34.8 |
| Levodopa | 34.8 |
| Carbidopa | 9.4 |
| Starch | 2.7 |
| Lactose | 6.3 |
| Hydroxypropyl methyl cellulose | 10.0 |
| Magnesium stearate | 1.0 |
| Talc | 1.0 |

Procedure: Entacapone, carbidopa, levodopa, starch and lactose were co-sifted to form bulk. Hydroxypropyl methylcellulose was sifted and mixed with bulk. A part of magnesium stearate was sifted and mixed with bulk. The bulk was dry granulated using roller compactor to form the slugs and the slugs were size reduced. The remaining portion of magnesium stearate and talc were sifted and added to the size reduced granules to form a bulk. The bulk was compressed using suitable punches to form tablets.

TABLE 17

Dissolution data of composition prepared as per example I.

| Time (hrs) | % Dissolved Entacapone | % Dissolved Levodopa | % Dissolved Carbidopa |
|---|---|---|---|
| 0.5 | 26 | 33 | 35 |
| 1 | 48 | 59 | 62 |
| 2 | 74 | 79 | 79 |

TABLE 17-continued

Dissolution data of composition prepared as per example I.

| Time (hrs) | % Dissolved | | |
|---|---|---|---|
| | Entacapone | Levodopa | Carbidopa |
| 3 | 86 | 92 | 94 |
| 4 | 93 | 102 | 101 |

Table 17 provides the dissolution data of composition prepared as per formula given in table 16. For determination of drug release rate of entacapone, USP Type 2 Apparatus (rpm 75) was used wherein 1000 ml of pH 5.5 phosphate buffer at 37° C.±0.5° C. was used as medium. Further, for determination of drug release rate of levodopa and carbidopa, USP Type 2 Apparatus (rpm 75) was used wherein 1000 ml of 0.1 N HCl at 37° C.±0.5° C. was used as medium.

Example-IX

TABLE 18

Pharmaceutical composition of the invention

| Ingredients | % w/w |
|---|---|
| Entacapone | 35.7 |
| Levodopa | 35.7 |
| Carbidopa | 9.6 |
| Mannitol | 5.3 |
| Microcrystalline cellulose | 2.5 |
| Poly vinyl pyrrolidone | 8.5 |
| Water | q.s. |
| Magnesium stearate | 1.4 |
| Talc | 1.3 |

Procedure: Entacapone, carbidopa, levodopa, starch and lactose were co-sifted and mixed to form bulk. Poly vinyl pyrrolidone was dissolved in water to form binder solution. The bulk was granulated using binder solution to from the granules and the granules were dried. The granules were size reduced. Magnesium stearate and talc were sifted and mixed with the size-reduced granules. The bulk was compressed using suitable punches to form tablets.

TABLE 19

Dissolution data of composition prepared as per example II.

| Time (hrs) | % Dissolved | | |
|---|---|---|---|
| | Entacapone | Levodopa | Carbidopa |
| 0.5 | 36 | 42 | 41 |
| 1 | 60 | 62 | 62 |
| 2 | 78 | 80 | 82 |
| 3 | 90 | 92 | 92 |
| 4 | 94 | 99 | 100 |

Table 19 provides the dissolution data of composition prepared as per formula given in table 18. For determination of drug release rate of entacapone, USP Type 2 Apparatus (rpm 75) was used wherein 1000 ml of pH 5.5 phosphate buffer at 37° C.±0.5° C. was used as medium. Further, for determination of drug release rate of levodopa and carbidopa, USP Type 2 Apparatus (rpm 75) was used wherein 1000 ml of 0.1 N HCl at 37° C.±0.5° C. was used as medium.

Example-X

TABLE 20

Pharmaceutical composition of the invention

| Ingredients | % w/w |
|---|---|
| Entacapone ER Layer | |
| Entacapone | 32.4 |
| Lactose | 7.7 |
| Hydroxypropyl methyl cellulose K100LVP | 5.7 |
| Hydroxypropyl methyl cellulose E-50 | 4.4 |
| Magnesium Stearate | 0.6 |
| Talc | 0.6 |
| Carbidopa - Levodopa ER Layer | |
| Levodopa | 32.4 |
| Carbidopa | 8.7 |
| Microcrystalline Cellulose | 2.9 |
| Hydroxypropyl methyl cellulose | 3.6 |
| Magnesium stearate | 0.7 |
| Talc | 0.2 |

Procedure: Entacapone ER Layer Granules

Entacapone, lactose and hydroxypropyl methyl cellulose were co-sifted to form a bulk. Magnesium stearate and talc were sifted and mixed with bulk. The bulk was dry granulated using roller compactor to form the slugs and the slugs were size reduced.

Levodopa-Carbidopa ER Layer Granules

Levodopa, carbidopa, microcrystalline cellulose, hydroxypropyl methyl cellulose were co sifted to form a bulk. Magnesium stearate and talc were sifted and mixed with the bulk. The bulk was dry granulated using roller compactor to form the slugs and the slugs were size reduced.

Compression

The entacapone ER layer granules and levodopa-carbidopa ER layer granules were compressed to form a bilayer tablet.

TABLE 21

Dissolution data of composition prepared as per example III.

| Time (hrs) | % Dissolved | | |
|---|---|---|---|
| | Entacapone | Levodopa | Carbidopa |
| 0.5 | 25 | 33 | 34 |
| 1 | 44 | 52 | 54 |
| 2 | 72 | 83 | 83 |
| 3 | 85 | 96 | 95 |
| 4 | 93 | 100 | 102 |

Table 21 provides the dissolution data of composition prepared as per formula given in table 20. For determination of drug release rate of entacapone, USP Type 2 Apparatus (rpm 75) was used wherein 1000 ml of pH 5.5 phosphate buffer at 37° C.±0.5° C. was used as medium. Further, for determination of drug release rate of levodopa and carbidopa, USP Type 2 Apparatus (rpm 75) was used wherein 1000 ml of 0.1 N HCl at 37° C.±0.5° C. was used as medium.

Example-XI

TABLE 22

Pharmaceutical composition of the invention

| Ingredients | % w/w |
|---|---|
| Entacapone ER Layer | |
| Entacapone | 33.3 |
| Microcrystalline cellulose | 4.0 |
| Lactose | 4.3 |
| Povidone | 3.0 |
| Hydroxypropyl cellulose | 3.8 |
| Water | q.s. |
| Magnesium Stearate | 1.0 |
| Talc | 0.7 |
| Carbidopa - Levodopa ER Layer | |
| Levodopa | 33.3 |
| Carbidopa | 9.0 |
| Lactose | 3.0 |
| Povidone | 2.9 |
| Water | q.s. |
| Magnesium stearate | 1.0 |
| Talc | 0.6 |

Procedure: Entacapone ER Layer Granules

Entacapone, microcrystalline cellulose and lactose were co sifted. Povidone was dissolved in water and the bulk was wet granulated with povidone solution to form granules and the granules were dried. The granules were size reduced. Hydroxypropyl cellulose was sifted and added to the size reduced granules. The bulk was lubricated with magnesium stearate and talc.

Levodopa-Carbidopa ER Layer Granules

Levodopa, carbidopa and lactose were co sifted to form a bulk. Povidone was dissolved in water and the bulk was wet granulated with povidone solution to form granules and the granules were dried. The granules were size reduced. The bulk was lubricated with magnesium stearate and talc.

Compression

The entacapone ER layer granules and levodopa-carbidopa ER layer granules were compressed to form a bilayer tablet.

TABLE 23

Dissolution data of composition prepared as per example IV.

| | % Dissolved | | |
|---|---|---|---|
| Time (hrs) | Entacapone | Levodopa | Carbidopa |
| 0.5 | 35 | 32 | 30 |
| 1 | 51 | 52 | 52 |
| 2 | 77 | 80 | 81 |
| 3 | 93 | 89 | 92 |
| 4 | 96 | 97 | 99 |

Table 23 provides the dissolution data of composition prepared as per formula given in table 22. For determination of drug release rate of entacapone, USP Type 2 Apparatus (rpm 75) was used wherein 1000 ml of pH 5.5 phosphate buffer at 37° C.±0.5° C. was used as medium. Further, for determination of drug release rate of levodopa and carbidopa, USP Type 2 Apparatus (rpm 75) was used wherein 1000 ml of 0.1 N HCl at 37° C.±0.5° C. was used as medium.

We claim:

1. An extended release pharmaceutical composition comprising from about 200 mg to about 1000 mg of entacapone or salts thereof, the entacapone being coated by or embedded in matrix with one or more hydrophilic or hydrophobic polymers for achieving extended release along with other pharmaceutically acceptable excipients selected from the group consisting of diluents, binders, disintegrants, lubricants and glidants; wherein the hydrophilic or hydrophobic polymers are selected from the group consisting of cellulose acetate propionate, ethyl cellulose, an alkyl alcohol, a wax, rosin, zein (prolamine from corn), povidone, kollidon SR, polyuronic acid salts, gellan gum, alkali metal salts of alginic acid or pectic acid, hydroxypropyl cellulose, hydroxy ethyl cellulose, hydroxypropyl methyl cellulose, polymerized gelatin, methacrylic acid copolymer type C NF, cellulose butyrate phthalate, cellulose hydrogen phthalate, cellulose propionate phthalate, polyvinyl acetate phthalate (PVAP), hydroxypropyl methylcellulose acetate, dioxypropyl methylcellulose succinate, carboxymethyl ethyl cellulose (CMEC), acrylic acid polymers and copolymers, methyl acrylate, ethyl acrylate, methyl methacrylate and/or ethyl methacrylate with copolymers of acrylic and methacrylic acid esters, Eudragit NE, Eudragit RL and, Eudragit RS; wherein the composition is an extended release pharmaceutical, which extends the release of entacapone or salts thereof from about 4 hours to about 6 hours.

2. The pharmaceutical composition of claim 1, wherein the composition comprises one or more of tablet, bilayered tablet, trilayered tablet, capsule, powder, disc, caplet, granules, pellets, granules in capsule, minitablets, minitablets in capsule, pellets in capsule, or sachet.

3. The pharmaceutical composition of claim 1, wherein one tablet of said composition exhibits no significant difference in rate and/or extent of absorption of entacapone as compared to 2 tablets of 200 mg immediate release entacapone commercially marketed as Comtan® administered at the interval of 3-4 hours.

4. The pharmaceutical composition of claim 1, wherein the said composition is extended release which exhibits a dissolution profile such that within 60 minutes at least 15% of entacapone is released, wherein the release rate is measured in Apparatus 2 (USP, Dissolution, paddle, 75 rpm) using 1000 ml of pH 5.5 phosphate buffer at 37° C.±0.5° C.

5. The pharmaceutical composition of claim 1, wherein the said composition is extended release which exhibits a dissolution profile such that within 4 hrs at least 60% of entacapone is released, wherein the release rate is measured in Apparatus 2 (USP, Dissolution, paddle, 75 rpm) using 1000 ml of pH 5.5 phosphate buffer at 37° C.±0.5° C.

6. The pharmaceutical composition of claim 1, further comprising from about 30 mg to about 300 mg of levodopa, and 10 mg to about 100 mg of carbidopa or salts thereof.

7. The pharmaceutical composition of claim 6, wherein said composition is extended release which exhibits a dissolution profile such that within 60 minutes at least 15% of entacapone or at least 15% of levodopa or at least 15% of carbidopa is released, wherein the release rate is measured in Apparatus 2 (USP, Dissolution, paddle, 75 rpm) using 1000 ml of pH 5.5 phosphate buffer at 37° C.±0.5° C.

8. The pharmaceutical composition of claim 6, wherein said composition is extended release which exhibits a dissolution profile such that within 4 hrs at least 60% of entacapone or at least 60% of levodopa or at least 60% of carbidopa is released, wherein the release rate is measured in Apparatus 2 (USP, Dissolution, paddle, 75 rpm) using 1000 ml of pH 5.5 phosphate buffer at 37° C.±0.5° C.

9. An extended release pharmaceutical composition comprising:

| Ingredients | % w/w |
|---|---|
| Entacapone | 60.1 |
| Mannitol | 18.0 |
| Hydroxypropyl methyl cellulose | 16.2 |
| Povidone | 0.9 |
| Magnesium Stearate | 0.9 |
| Talc | 0.2-3 |
| Coating | |
| Opadry | 3.8. |

10. An extended release pharmaceutical composition comprising:

| Ingredients | % w/w |
|---|---|
| Entacapone | 57.1 |
| Lactose | 19.3 |
| Hydroxy ethyl cellulose | 12.4 |
| Hydroxypropyl methyl cellulose | 8.6 |
| Water | q.s. |
| Magnesium Stearate | 1.4 |
| Talc | 1.1. |

11. An extended release pharmaceutical composition comprising:

| Ingredients | % w/w |
|---|---|
| Entacapone | 74.1 |
| Microcrystalline cellulose | 10.7 |
| Kollidon SR | 13.3 |
| Magnesium Stearate | 1.1 |
| Talc | 0.7. |

12. An extended release pharmaceutical composition comprising:

| Ingredients | % w/w |
|---|---|
| Entacapone | 34.8 |
| Levodopa | 34.8 |
| Carbidopa | 9.4 |
| Starch | 2.7 |
| Lactose | 6.3 |
| Hydroxypropyl methyl cellulose | 10.0 |
| Magnesium stearate | 1.0 |
| Talc | 1.0. |

13. An extended release pharmaceutical composition comprising:

| Ingredients | % w/w |
|---|---|
| Entacapone | 35.7 |
| Levodopa | 35.7 |
| Carbidopa | 9.6 |
| Mannitol | 5.3 |
| Microcrystalline cellulose | 2.5 |
| Poly vinyl pyrrolidone | 8.5 |
| Water | q.s. |
| Magnesium stearate | 1.4 |
| Talc | 1.3. |

14. An extended release pharmaceutical composition comprising:

| Ingredients | % w/w |
|---|---|
| Entacapone ER Layer | |
| Entacapone | 32.4 |
| Lactose | 7.7 |
| Hydroxypropyl methyl cellulose K100LVP | 5.7 |
| Hydroxypropyl methyl cellulose E-50 | 4.4 |
| Magnesium Stearate | 0.6 |
| Talc | 0.6 |
| Carbidopa- Levodopa ER Layer | |
| Levodopa | 32.4 |
| Carbidopa | 8.7 |
| Microcrystalline Cellulose | 2.9 |
| Hydroxypropyl methyl cellulose | 3.6 |
| Magnesium stearate | 0.7 |
| Talc | 0.2. |

15. An extended release pharmaceutical composition comprising:

| Ingredients | % w/w |
|---|---|
| Entacapone ER Layer | |
| Entacapone | 33.3 |
| Microcrystalline cellulose | 4.0 |
| Lactose | 4.3 |
| Povidone | 3.0 |
| Hydroxypropyl cellulose | 3.8 |
| Water | q.s. |
| Magnesium Stearate | 1.0 |
| Talc | 0.7 |
| Carbidopa- Levodopa ER Layer | |
| Levodopa | 33.3 |
| Carbidopa | 9.0 |
| Lactose | 3.0 |
| Povidone | 2.9 |
| Water | q.s. |
| Magnesium stearate | 1.0 |
| Talc | 0.6. |

* * * * *